(12) United States Patent
Angelopoulos et al.

(10) Patent No.: US 7,998,198 B2
(45) Date of Patent: Aug. 16, 2011

(54) ACCOMMODATIVE IOL WITH DYNAMIC SPHERICAL ABERRATION

(75) Inventors: Robert Angelopoulos, Fort Worth, TX (US); Xin Hong, Fort Worth, TX (US); Xiaoxiao Zhang, Fort Worth, TX (US); Mutlu Karakelle, Fort Worth, TX (US)

(73) Assignee: Novartis AG, Basel (CH)

( * ) Notice: Subject to any disclaimer, the term of this patent is extended or adjusted under 35 U.S.C. 154(b) by 270 days.

(21) Appl. No.: 12/365,609

(22) Filed: Feb. 4, 2009

(65) Prior Publication Data

US 2009/0204211 A1 Aug. 13, 2009

Related U.S. Application Data

(60) Provisional application No. 61/026,939, filed on Feb. 7, 2008.

(51) Int. Cl.
*A61F 2/16* (2006.01)
(52) U.S. Cl. .............. 623/6.37; 623/6.32; 623/6.34; 623/6.38; 623/6.4
(58) Field of Classification Search .......... None
See application file for complete search history.

(56) References Cited

U.S. PATENT DOCUMENTS

| 4,696,569 | A | 9/1987 | Geary et al. |
| 5,935,738 | A | 8/1999 | Yasuzato et al. |
| 6,616,691 | B1 | 9/2003 | Tran |
| 7,316,713 | B2 | 1/2008 | Zhang |
| 2005/0060032 | A1 | 3/2005 | Magnante et al. |
| 2007/0078515 | A1 | 4/2007 | Brady |
| 2007/0106377 | A1 | 5/2007 | Smith et al. |

FOREIGN PATENT DOCUMENTS

| DE | 10 2006 021521 | 11/2007 |
| WO | WO 2007/015640 | 2/2007 |
| WO | WO 2007/027091 | 3/2007 |
| WO | WO 2007/047427 | 4/2007 |

OTHER PUBLICATIONS

U.S. Appl. No. 11/000,770, filed Dec. 1, 2004, Simpson.
International Search Report for PCT/US2009/033378, Publication No. WO2009100322, 8 pages.

*Primary Examiner* — David H Willse
*Assistant Examiner* — Javier G Blanco
(74) *Attorney, Agent, or Firm* — Jonathan E. Prejean (57) ABSTRACT

The present invention is generally directed to accommodative intraocular lenses (IOLs) that exhibit a dynamic spherical aberration as a function of accommodative power. By way of example, in one aspect, the present invention provides an intraocular lens (IOL) having an anterior optical element, a posterior optical element, and a mechanism for coupling the anterior and posterior elements so as to allow axial movement of those elements relative to one another for providing accommodation when the lens is implanted in a patient's eye. Each of the anterior and the posterior elements includes at least one aspherical surface, where the asphericities of the surfaces are adapted to provide a combined spherical aberration that varies with accommodation.

16 Claims, 5 Drawing Sheets

ACCOMMODATIVE IOL WITH DYNAMIC SPHERICAL ABERRATION

RELATED APPLICATIONS

This application claims priority under 35 USC §119 to U.S. provisional application Ser. No. 61/026,939, filed on Feb. 7, 2008.

BACKGROUND

The present invention relates generally to ophthalmic lenses, and more particularly to accommodative intraocular lenses (IOLs) exhibiting dynamic aberrations.

The optical power of the eye is determined by the optical power of the cornea and that of the crystalline lens, with the lens providing about a third of the eye's total optical power. The lens is a transparent, biconvex structure whose curvature can be changed by ciliary muscles for adjusting its optical power so as to allow the eye to focus on objects at varying distances. This process is known as accommodation. As a result of accommodation, spherical aberration exhibited by the natural lens shifts in the negative direction.

The natural lens, however, becomes less transparent in individuals suffering from cataract, e.g., due to age and/or disease, thus diminishing the amount of light that reaches the retina. A known treatment for cataract involves removing the opacified natural lens and replacing it with an artificial intraocular lens (IOL). Although such IOLs can improve the patient's vision, they can, however, lead to the loss, or at least severe curtailment, of the eye's accommodative ability. In particular, a class of IOLs, commonly referred to as monofocal IOLs, provide a single optical power and hence do not allow accommodation. Another class of IOLs, commonly known as diffractive IOLs, provide primarily two optical powers, typically a far and a near optical power. As such, these IOLs provide only a limited degree of accommodation, commonly known as pseudoaccommodation.

Dual-optic accommodative IOLs are also known that utilize the movement of two optical elements relative to one another in response to the movement of the ciliary muscles to provide a degree of continuous accommodation. However, the range of movement of the two optics of such IOLs is typically limited, thus restricting the range of viewing distance over which they provide accommodation.

Accordingly, there is a need for enhanced IOLs, and particularly improved accommodative IOLs as well as for methods of correcting vision that utilize them.

SUMMARY

In one aspect, the present invention provides an intraocular lens (IOL) having an anterior optical element, a posterior optical element, and a mechanism for coupling the anterior and posterior elements so as to allow axial movement of those elements relative to one another for providing accommodation when the lens is implanted in a patient's eye. Each of the anterior and the posterior elements includes at least one aspherical surface, where the asphericities of the surfaces are adapted to provide a combined spherical aberration that varies with accommodation.

In a related aspect, the spherical aberration exhibited by the IOL, as result of the combined aberration of the anterior and the posterior elements, changes from a positive value to a negative value in response to a change in the pupil size of the eye in which the IOL is implanted as the eye accommodates from distance vision to near vision. By way of example, the spherical aberration can vary over a range of about +0.2 µm to about −0.5 µm (minus 0.5 microns) as the pupil diameter changes from about 6 mm to about 1.5 mm during accommodation. In some cases, such a dynamic variation of the IOL's spherical aberration can also be characterized as a change over a range of about +0.2 µm to about −0.5 µm (minus 0.5 microns) as the IOL optical power varies over a range of about 0 to about 6 D due to accommodation. In some other cases, the range of the dynamic variation can be even bigger to further increase the depth of focus.

In a related aspect, the IOL can exhibit a slight positive spherical aberration when the IOL's optical elements are separated by a distance corresponding to an accommodative state suitable for distance vision. Such a positive spherical aberration can be, e.g., in a range of about +0.2 µm to about 0 µm. In contrast, the IOL can exhibit a negative spherical aberration when the IOL's optical elements are separated by a distance corresponding to an accommodative state that is suitable for near vision. By way of example, such a negative spherical aberration can be in a range of about −0.5 µm (minus 0.5 microns) to about 0 µm.

In other cases, the IOL can exhibit a slight negative spherical aberration when the eye is in a dis-accommodative state (a state suitable for distance vision), e.g., a spherical aberration in a range of about −0.5 µm (minus 0.5 microns) to about 0 µm, with the spherical aberration becoming progressively more negative as the eye accommodates to see ever closer objections.

In a related aspect, the anterior optical element provides a monofocal refractive optical power in a range of about 6 D to about 40 D while the posterior optical element provides a monofocal refractive optical power in a range of about −30 D (minus 30 D) to about −3 D (minus 3 D).

In another aspect, an intraocular lens (IOL) assembly is disclosed that includes an anterior lens, a posterior lens and a coupling mechanism that connects those lenses so as to cause their axial movement relative to one another in response to the natural accommodative forces of the eye when the IOL assembly is implanted in a patient's eye. The lenses provide a combined spherical aberration that varies as a function of the accommodative state of the eye. For example, the combined spherical aberration changes from a positive value to a negative value as the eye's accommodative state varies from one suitable for distance vision to one suitable for near vision. Alternatively, the combined spherical aberration can be negative for the entire range of accommodative power with the aberration decreasing (becoming more negative) as the accommodative power increases. In some cases, such a decrease can be characterized by a substantially linear slope in a spherical aberration vs. accommodation plot.

In another aspect, an accommodative intraocular lens (IOL) is disclosed that comprises a dual-element optic having an anterior optical element and a posterior optical element, where each element provides a spherical aberration such that a combined spherical aberration of those elements varies as a function of an accommodative state of the eye in which the optic is implanted. By way of example, the combined spherical aberration can vary over a range extending from about +0.2 µm (plus 0.2 microns) to about −0.5 µm as the accommodation state of the eye varies from one suitable for distance vision to one suitable for near vision.

In another aspect, the invention provides an intraocular lens (IOL) that comprises an anterior optical element having at least one aspherical surface, and a posterior optical element having at least one aspherical surface, where the aspherical surfaces are adapted to provide a combined spherical aberration that varies as a function of the pupil size when the lens is implanted in a patient's eye. For example, in some cases, the combined spherical aberration is positive for a pupil size equal or greater than about 6 mm and is negative for a pupil size less than about 1.5 mm.

In a related aspect, in the above IOL, the anterior optical element provides a monofocal optical power in a range of about 6 to about 40 D, and the posterior optical element provides a monofocal optical power in a range of about −30 D (minus 30 D) to about −3 D (minus 3 D).

In another aspect, a method of correcting vision is disclosed that includes providing an accommodative intraocular lens (IOL) exhibiting a variable spherical aberration that is adapted to vary as a function of an accommodative state of eye in which the IOL is implanted, and implanting the IOL in a patient's eye.

Further understanding of the invention can be obtained by reference to the following detailed description in connection with the associated drawings, which are discussed briefly below.

DETAILED DESCRIPTION

The present invention generally provides accommodative intraocular lenses (IOLs) that exhibit a dynamic spherical aberration as a function of the accommodative state of the eye so as to enhance the effective accommodative power. By way of example, the IOL can include two optics separated by an adjustable axial distance and coupled to one another via a mechanism that can change the axial distance in response to the natural accommodative forces of the eye, thereby providing an accommodative power. At least one surface of each optic can exhibit an aspherical profile such that the IOL provides a spherical aberration that decreases as a function of increased accommodation. For example, the spherical aberration can exhibit a variation characterized by a negative slope with increased accommodation, that is, the aberration can become progressively more negative as the eye accommodates to see closer objects.

Although in the embodiments discussed above the dynamic aberration of the IOL is described in connection with spherical aberration, the teachings of the invention can apply to dynamically vary other types of aberration, such as astigmatic and/or cylindrical aberrations, in an accommodative IOL as a function of accommodation. For example, in some embodiments, at least one IOL of a dual-optic accommodative IOL can include a cylindrical surface that is designed to minimize, e.g., fully correct, the eyes cylindrical aberration (e.g., by counteracting a cylindrical aberration of the cornea) for far vision. As the eye accommodates to view closer objects, the axial separation between the two optics of the IOL can change, thus resulting in a residual cylindrical aberration. For example, rather than fully correcting the cylindrical error of the cornea, the cylindrical surface generates a targeted residual cylindrical aberration for near vision and expands the depth of focus range, thereby leading to a varying residual cylindrical aberration. In other words, the IOL provides a cylindrical aberration that changes dynamically as a function of increased accommodation.

Moreover, although in many embodiments discussed below a dynamic change in an aberration is achieved due to a change in an axial separation of the two optics, in other embodiments such dynamic variation of one or more aberrations can be achieved as a result of a lateral shift on top of the axial separation between the two optics of an accommodative IOL.

Figure 1:
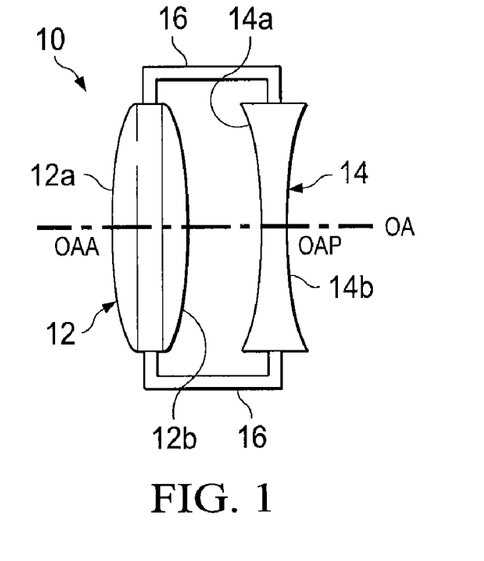
FIG. 1 is a schematic side view of an accommodative IOL in accordance with an embodiment of the invention having an anterior lens and a posterior lens coupled to one another by a mechanism for moving the lenses axially relative to one another, FIG. 2A schematically depicts the anterior lens of the IOL shown in FIG. 1 illustrating that it includes an aspheric posterior surface FIG. 2B schematically depicts the posterior lens of the IOL shown in FIG. 1 illustrating that it includes an aspheric anterior surface.

FIG. 1 schematically depicts an intraocular lens (IOL) 10 according to an embodiment of the invention that includes an anterior optical element 12 (e.g., a lens) and a posterior optical element 14 (e.g., another lens) that are positioned at an axial distance relative to one another. As discussed further below, when the IOL is implanted in a patient's eye, the axial distance between the two elements can vary in response to the natural accommodative forces of the eye so as to change the combined power of the elements for providing accommodation. The anterior optical element 12 is disposed about its optical axis OAA and the posterior optical element 14 is disposed about its respective optical axis OAP. In this case, the optical axes of the two elements are colinear. Hence, in the following description reference will be made to an optical axis OA of the IOL 10.

An accommodative mechanism 16 couples the anterior and the posterior optical elements together so as to allow their relative axial movement (a movement along the optical axis OA) when the IOL is implanted in a patient's eye in response to the natural accommodative forces of the eye. While in some embodiments the mechanism causes one of the optical elements (e.g., the anterior element 12) to move while the other remains stationary, in other embodiments the mechanism 16 causes the movement of both elements. The relative movement of the optical elements varies the axial separation distance between those elements, thereby changing the optical power of the IOL. In other words, the change in the axial distance can provide accommodation for viewing objects at different distances from the eye, as discussed further below.

The anterior and posterior optical elements as well as the accommodative mechanism can be formed of any suitable biocompatible material. Some examples of such materials include, without limitation, hydrogel, silicone, polymethylmethacrylate (PMMA), and a polymeric material known as Acrysof (a cross-linked copolymer of 2-phenylethyl acrylate and 2-phenylethyl methacrylate). By way of example, in some cases, the anterior and the posterior optical elements are formed of one type of a biocompatible polymeric material and the accommodative mechanism is formed of another type.

In this embodiment, the anterior optical element 12 has a bi-convex profile and functions as a lens providing a positive optical power and the posterior optical element 14 has a bi-concave profile and functions as a lens providing a negative optical power. In some embodiments, the curvatures of the surfaces of each element together with the material forming that element can be selected such that the anterior optical element provides an optical power in a range of about 6 to about 40 Diopters (D), or more preferably in a range of about 15 to about 35 D, and the posterior optical element provides an optical power in a range of about −30 D to about −3 D, and more preferably in a range of about −25 D to about −5 D. By way of example, the optical power of the two elements can be selected such that the combined power of the IOL for viewing distant objects (e.g., objects at a distance greater than about 2000 cm from the eye), i.e., far-vision power, is in a range of about 6 to about 34 D. This far-vision power of the IOL can be achieved at the minimum separation of the two optical elements from one another. As the axial distance between the elements increases due to accommodative forces, the optical power of the IOL increases until a maximum optical power is reached for viewing objects at distances equal or less than about 40 cm (i.e., near vision). This maximum optical add power can be, e.g., in a range of about 0.1 to about 5 D.

The anterior optical element 12 includes an anterior surface 12a and a posterior surface 12b. Similarly, the posterior optical element 14 includes an anterior surface 14a and a posterior surface 14b. As discussed further below, in this embodiment, each of the posterior surface 12b of the anterior element 12 and the anterior surface 14a of the posterior element 14 exhibits an aspheric profile, whereas the anterior surface of the anterior element and the posterior surface of the posterior element have substantially spherical profiles. The term "aspheric profile," as used herein, generally refers to a surface profile that exhibits deviations from a surface profile that corresponds to a portion of a sphere. While in some embodiments, such aspheric deviations can be rotationally symmetric about a symmetry axis of the surface (e.g., optical axis of the lens), in other embodiments the deviations may not exhibit such rotational symmetry.

The asphericity of the surface 12b and that of the surface 14a are configured such that they cooperatively provide a combined spherical aberration that varies as a function of axial distance between the two elements, or more generally as a function of the pupil size, as discussed further below. In other embodiments, surfaces of the IOL 10 other than the aforementioned surfaces 12b and 14a can exhibit a selected degree of asphericity. More generally, at least one of the surfaces of each optical element exhibits a selected asphericity such that they cooperatively provide a combined spherical aberration that varies as a function of the pupil size, which can vary as a result of accommodation, as discussed below.

More specifically, the spherical aberration exhibited by the IOL can decrease as the pupil diameter decreases as a result of increasing accommodation (which can correspond to an increase in the axial separation of the IOL's optics). For example, in some cases, the IOL can exhibit a small positive spherical aberration when the eye is in a dis-accommodative state for viewing distance objects. As the eye accommodates to focus on closer objects, the spherical aberration decrease and changes to a negative value at a given accommodative power. As the eye accommodates even further, the spherical aberration becomes progressively more negative. In some other cases, the spherical aberration exhibited by the IOL for far-vision is slightly negative and it becomes progressively more negative with increased accommodation.

Figure 2A:
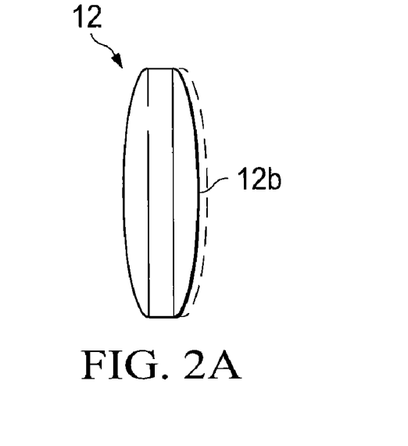
Figure 2B:
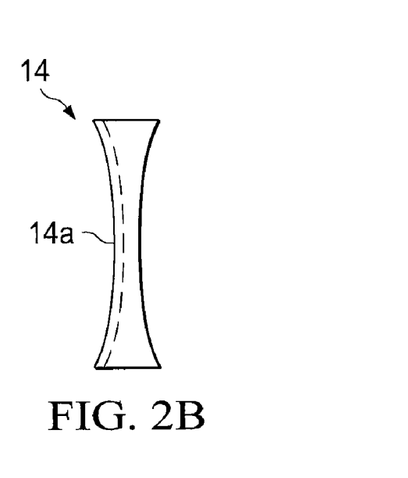

By way of further illustration, as shown schematically in FIG. 2A, the posterior surface 12b of the anterior element 12 exhibits a surface profile that substantially coincides with a putative spherical profile (shown by dashed lines) at radial distances close to the optical axis and progressively deviates from the putative profile as a function of increasing radial distance from the optical axis. Similarly, as depicted schematically in FIG. 2B, the anterior surface 14a of the posterior element 14 exhibits a deviation from a putative spherical profile (shown by dashed lines).

As noted above, the asphericity of the surfaces are chosen such that the combined spherical aberration exhibited by the two elements varies as a function of the pupil size. For example, in some embodiments, the radial surface profiles of the aspherical surfaces of the anterior and the posterior optics of the IOL 10 can be defined by the following relation:

$$x = \frac{cr^2}{1 + \sqrt{1 - (1+k)c^2 r^2}} + a_1 r^2 + a_2 r^4 + a_3 r^6 \qquad \text{Eq. (1)}$$

wherein, z denotes a sag of the surface at a radial distance r from an optical axis of the lens, c denotes curvature of the surface at its apex (at the intersection of the optical axis with the surface); c=1/r where r denotes the radial point on the surface as measured from the apex, k denotes a conic constant, $a_1$ denotes a second order aspheric coefficient, $a_2$ denotes a fourth order aspheric coefficient, and $a_3$ denotes a sixth order aspheric coefficient.

For the posterior surface 12b of the anterior element 12, in some embodiments, c can be in a range of about −6 to about −15 mm$^{-1}$, k can be in a range of about −20 to about −60, $a_1$ can be in a range of about −1E-2 to about 1E-2, $a_2$ can be in a range of about −1E-2 to about 1E-2, and $a_3$ can be in a range of about −1E-2 to about 1E-2. For the anterior surface 14a of the posterior element 14, in some embodiments, c can be in a range of about −60 to about 60, k can be in a range of about −20 to about −60, $a_1$ can be in a range of about −1E-2 to about 1E-2, $a_2$ can be in a range of about −1E-2 to about 1E-2, and $a_3$ can be in a range of about −1E-2 to about 1E-2.

By way of further illustration, Tables 1A and 1B below present exemplary design parameters for three hypothetical dual-element accommodative IOLs in accordance with some embodiments of the invention together with the design parameters of the anterior lens (Table 1A) as well as the posterior lens (Table 1B) of such IOLs.

TABLE 1A

| Overall IOL Power (D) | Anterior Lens Power (D) | Posterior Lens Power (D) | Anterior Lens | | | | CT (mm) | ET (mm) |
| --- | --- | --- | --- | --- | --- | --- | --- | --- |
| | | | Anterior Radius (mm) | Posterior Radius (mm) | Posterior Surface CC | Posterior Asphere | | |
| 15.0 | 37.0 | −23.1 | 11.183 | −11.904 | −43.937 | −1.142E−03  8.943E−05 | 0.905 | 0.210 |
| 21.0 | 37.0 | −16.8 | 11.183 | −11.904 | −43.937 | −1.142E−03  8.943E−05 | 0.905 | 0.210 |
| 34.0 | 37.0 | −3.0 | 11.183 | −11.904 | −43.937 | −1.142E−03  8.943E−05 | 0.905 | 0.210 |

TABLE 1B

| Overall IOL Power (D) | Anterior Lens Power (D) | Posterior Lens Power (D) | Posterior Lens | | | CT (mm) | ET (mm) |
| --- | --- | --- | --- | --- | --- | --- | --- |
| | | | Anterior Radius (mm) | Posterior Radius (mm) | Anterior Surface CC | | |
| 15.0 | 37.0 | −23.1 | −6.016 | −17.197 | −3.788 | 0.905 | 0.210 |
| 21.0 | 37.0 | −16.8 | −6.881 | −14.968 | −4.472 | 0.905 | 0.210 |
| 34.0 | 37.0 | −3.0 | −13.930 | −17.417 | −17.458 | 0.905 | 0.210 |

In use, the IOL 10 can be implanted in a patient's eye to replace an occluded natural lens. During a cataract surgery, a small incision is made in the cornea, e.g., by utilizing a diamond blade. An instrument is then inserted through the corneal incision to cut a portion of the anterior lens capsule, typically in a circular fashion, to provide access to the opacified natural lens. An ultrasound or a laser probe is then employed to break up the lens, and the resulting lens fragments are aspirated. The IOL can then be inserted in the patient's capsular bag to be placed against the posterior side of the capsular bag. In some cases, the posterior element of the IOL coupled to the accommodative mechanism is first inserted into the capsular bag, and subsequently the anterior element is inserted and coupled to the accommodative mechanism. The accommodative mechanism engages with the capsular bag so as to respond to the natural accommodative forces of the eye. In some embodiments, the various components of the IOL assembly are foldable and can be inserted in the capsular bag by employing an injector. Once inside the eye, the components can unfold to assume their normal shapes.

For viewing a distant object (e.g., when the eye is in a dis-accommodative state to view objects at a distance greater than about 2000 cm from the eye), the eye's ciliary muscles relax to enlarge the ciliary ring diameter. The enlargement of the ciliary ring in turn causes an outward movement of the zonules, thereby flattening the capsular bag. In some embodiments, such flattening of the capsular bag can cause the accommodative mechanism 16 to move the anterior and the posterior optics toward each other, thereby lowering the optical power of the IOL. In contrast, to view closer objects (that is, when the eye is in an accommodative state), the ciliary muscles contract causing a reduction in the ciliary ring diameter. This reduction in diameter relaxes the outward radial force on the zonules to undo the flattening of the capsular bag. This can in turn cause the accommodative mechanism 16 to move the anterior and the posterior optics away from each other, thereby increasing the total optical power of the IOL 10.

It is known that the pupil diameter changes as the eye accommodates. In particular, as the eye accommodates to see closer objects the pupil diameter decreases. As noted above, the total spherical aberration exhibited by the IOL 10 decreases (e.g., it changes from a positive value to a negative value that progressively becomes more negative with increased accommodation) as the pupil size decreases, that is, as the eye accommodates to see closer objects. Negative spherical aberration causes the light at different radial locations across an optical aperture to focus at different points along the optical axis of the IOL. As the aperture decreases, the spherical aberration of the IOL causes the light to be focused closer to the IOL, thereby enhancing the effective power of the IOL. In other words, the IOL provides a dynamic spherical aberration that varies as a function of the eye's accommodative state to enhance accommodation.

As noted above, in some embodiments, the IOL 10 exhibits a relatively small positive spherical aberration for distance vision (e.g., in a range of about 0.1 to 0 μm). Alternatively, in other embodiments, the IOL 10 exhibits a relatively small negative spherical aberration for distance vision (e.g., in a range of about −0.1 to −0.2 μm). Such a negative or positive spherical aberration can improve the depth-of-focus for distance vision. As the eye accommodates to see closer objects, the pupil diameter decreases with a concomitant decrease in the spherical aberration exhibited by the IOL. For example, in the case of the embodiment having a small positive spherical aberration for far vision, the spherical aberration can change from a positive value to a negative value that progressively decreases to greater negative values as the eye accommodates to see ever closer objects. In the embodiments having a small negative spherical aberration for far vision, the spherical aberration takes on progressively negative values as the eye accommodates to see closer objects. As discussed above, such a negative spherical aberration can enhance accommodation. In addition, a natural increase in depth-of-focus can occur with a smaller pupil size.

The spherical aberration exhibited by an optical system, such as the exemplary IOL 10, can be measured by variety of known techniques. By way of example, U.S. Pat. No. 4,696,569 entitled "Method Of Measuring Spherical Aberration And Apparatus Therefor" as well as U.S. Pat. No. 5,935,738 entitled "Phase-Shifting Mask, Exposure Method And Method For Measuring Amount Of Spherical Aberration," both of which are herein incorporated by reference in their entirety, disclose methods and apparatus for measuring spherical aberration.

In some embodiments, at least one surface of the two optics comprising the IOL exhibits a toric profile. As is known in the art, a toric surface profile is characterized by two different radii of curvature corresponding to two orthogonal directions along the surface. By way of example, the toric profile can be selected in a manner known in the art to compensate for an astigmatic aberration of the patient's eye for distance vision. By way of example, a toric profile can be imparted to a posterior surface 12b of the anterior optic 12 of the IOL 10 shown in FIG. 1.

Figure 3A:
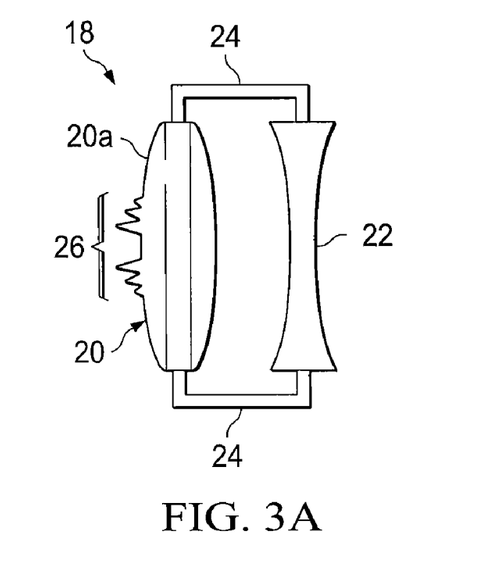
FIG. 3A is a schematic side view of a dual-optic accommodative IOL according to an embodiment of the invention having a diffractive structure on a surface of its anterior optic.

While in the above embodiments each of the two optical elements of the accommodative IOL provides a monofocal optical power, in other embodiments at least one of those optical elements can provide multiple optical powers, e.g., primarily two optical powers. By way of example, FIG. 3A schematically depicts an accommodative IOL 18 in accordance with such an embodiment having an anterior lens 20 and a posterior lens 22. An accommodative mechanism 24 couples the anterior lens 26 to the posterior lens to cause their axial movement relative to one another in response to natural accommodative forces of the eye when the IOL is implanted in a patient's eye. Similar to the previous embodiments, the anterior lens 20 has a bi-convex profile and the posterior lens 22 has a bi-concave profile. The posterior surface of the anterior lens and the anterior surface of the posterior lens exhibit a selected degree of asphericity to provide a dynamic spherical aberration as a function of accommodation (a spherical aberration that decreases as the patient accommodates to see closer objects), e.g., in a manner discussed above.

In this embodiment, however, a diffractive structure 26 is disposed on an anterior surface 20a of the anterior lens such that the anterior lens provides a far-focus optical power as well as a near-focus optical power. More specifically, the curvatures of the anterior and the posterior surfaces of the anterior lens, together with the index of refraction of the material forming that lens, impart to the lens a refractive optical power (herein referred to as the far-focus power). The diffractive structure in turn provides a zero$^{th}$ order power that corresponds substantially to this far-focus power, as well as a first order diffractive power that is greater than the zero$^{th}$ order power. The difference between the $1^{st}$ order and the zero$^{th}$ order optical powers is commonly referred to as the add power of the IOL.

In many embodiments, the far-focus power of the anterior lens can be in a range of about 6 D to about 40 D and its add power can be in a range of about 1 D to about 4 D, or more preferably in a range of about 2 D to about 4 D. Similar to the previous embodiments, the posterior lens provides a monofocal optical power that can be, e.g., in a range of about −30 to about −3 D. The far-focus power of the anterior lens together with the monofocal power of the posterior lens provide a primary power of the IOL. As the accommodative mechanism changes the separation distance between the anterior and the posterior lenses, this IOL's primary power can change from a power suitable for distance vision for one suitable for near vision. In some cases, this accommodative change in power can be in a range of about 0.5 to about 5 D.

The add power provided by the diffractive structure of the anterior lens 20 can enhance and/or augment the accommodative change in power achieved by axial movement of the anterior and posterior lenses. In some cases, the diffractive add power is selected to be within the range of accommodative power. In other cases, however, the add power can lie outside this range so as to augment the accommodation capability of the IOL. Some exemplar values for the add power can lie in a range of about 3 D to about 4 D.

Figure 3B:
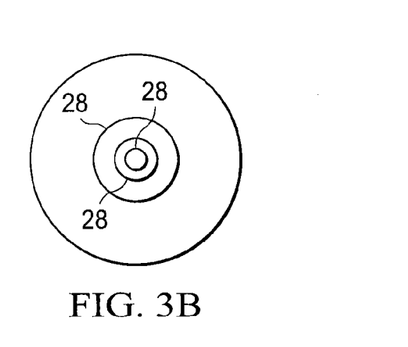
FIG. 3B is a schematic view of the surface of the anterior optic of the IOL of FIG. 3A depicting the diffractive structure.
Figure 3C:
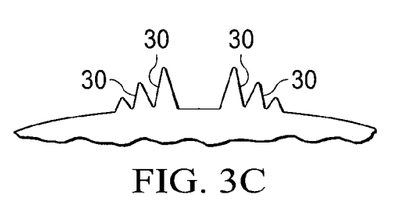
FIG. 3C is a schematic radial profile of the anterior surface of the IOL of FIG. 3A having a diffractive structure minus the base curvature of the surface.

The diffractive structure 26 can be implemented in a variety of different ways. Generally, as shown in FIGS. 3A and 3B, the diffractive structure 26 includes a plurality of diffractive zones 28 that are separated by a plurality of steps 30. While in some implementations, the step heights are substantially uniform, in others they can vary (e.g., decrease) as a function of increasing radial distance from the lens's optical axis (that is, the step heights are apodized). By way of example, a substantially uniform step height can be defined in accordance with the following relation:

$$\text{Step height} = \frac{\lambda}{\alpha(n_2 - n_1)} \quad \text{Equation (2)}$$

wherein $\lambda$ denotes a design wavelength (e.g., 550 nm), $\alpha$ denotes a parameter that can be adjusted to control diffraction efficiency associated with various orders, e.g., a can be selected to be 2.5;

$n_2$ denotes the index of refraction of the optic, $n_1$ denotes the refractive index of a medium in which the lens is placed By way of example, in some other cases, where the step heights decrease as a function of radial distance from the optical axis, the step heights can be defined in accordance with the following relation:

$$\text{Step height} = \frac{\lambda}{\alpha(n_2 - n_1)} f_{apodize} \quad \text{Equation (3)}$$

wherein $\lambda$ denotes a design wavelength (e.g., 550 nm), $\alpha$ denotes a parameter that can be adjusted to control diffraction efficiency associated with various orders, e.g., $\alpha$ can be selected to be 2.5;

$n_2$ denotes the index of refraction of the optic, $n_1$ denotes the refractive index of a medium in which the lens is placed, and $f_{apodize}$ represents a scaling function whose value decreases as a function of increasing radial distance from the intersection of the optical axis with the anterior surface of the lens. By way of example, the scaling function $f_{apodize}$ can be defined by the following relation:

$$f_{apodize} = 1 - \left(\frac{r_i}{r_{out}}\right)^3. \quad \text{Equation (4)}$$

wherein
$r_i$ denotes the radial distance of the $i^{th}$ zone,
$r_{out}$ denotes the outer radius of the last bifocal diffractive zone. Other apodization scaling functions can also be employed, such as those disclosed in a co-pending patent application entitled "Apodized Aspheric Diffractive Lenses," filed Dec. 1, 2004 and having a Ser. No. 11/000,770, which is herein incorporated by reference.

In some embodiments, the diffractive zones are in the form of annular regions that extend about the optic's optical axis. In some of such embodiments, the radial location of a zone boundary ($r_i$) is selected in accordance with the following relation:

$$r_i^2 = (2i+1)\lambda f \qquad \text{Equation (5)}$$

wherein
i denotes the zone number (i=0 denotes the central zone),
$r_i$ denotes the radial location of the ith zone,
$\lambda$ denotes the design wavelength, and
$f$ denotes an add power.

A variety of accommodative mechanisms known in the art can be utilized in various embodiments of the invention, such as the IOLs 10 and 18 shown in FIGS. 1 and 3A. An example of such a mechanism is disclosed in U.S. Pat. No. 7,316,713 entitled "Accommodative Intraocular Lens System." Another mechanism is disclosed in U.S. Pat. No. 6,616,691 entitled "Accommodative Intraocular Lens." Both of these patents are herein incorporated by reference in their entirety.

Example

The optical performance of exemplary hypothetical designs of dual-element accommodative IOLs according to some embodiments of the invention was theoretically compared with that of respective spherical designs as well as designs in which the spherical aberration was reduced.

The surface parameters of the design according to the teachings of the invention are given in the above Tables 1A and 1Bs. For the spherical designs, the surface parameters of the anterior lens as well as the posterior lens are given below in Tables 2A and 2B:

TABLE 2A

| Overall IOL Power (D) | Anterior Lens Power (D) | Posterior Lens Power (D) | Anterior Lens | | | |
|---|---|---|---|---|---|---|
| | | | Anterior Radius (mm) | Posterior Radius (mm) | CT (mm) | ET (mm) |
| 15.0 | 37.0 | −23.1 | 11.001 | −12.133 | 0.894 | 0.100 |
| 21.0 | 37.0 | −16.8 | 11.001 | −12.133 | 0.894 | 0.100 |
| 34.0 | 37.0 | −3.0 | 11.001 | −12.133 | 0.894 | 0.100 |

TABLE 2B

| Posterior Lens | | | |
|---|---|---|---|
| Anterior Radius (mm) | Posterior Radius (mm) | CT (mm) | ET (mm) |
| −6.424 | −20.989 | 0.143 | 0.500 |
| −7.995 | −21.466 | 0.126 | 0.500 |
| −16.438 | −21.466 | 0.245 | 0.300 |

Tables 3A and 3B below provide the surface parameters of the anterior and the posterior lenses of the theoretical IOL design in which the spherical aberration was minimized:

TABLE 3A

| Overall IOL Power (D) | Anterior Lens Power (D) | Posterior Lens Power (D) | Anterior Lens | | | | |
|---|---|---|---|---|---|---|---|
| | | | Anterior Radius (mm) | Posterior Radius (mm) | Posterior Surface CC | CT (mm) | ET (mm) |
| 15.0 | 37.0 | −23.1 | 12.374 | −10.788 | −6.414 | 0.850 | 0.100 |
| 21.0 | 37.0 | −16.8 | 12.374 | −10.788 | −6.414 | 0.850 | 0.100 |
| 34.0 | 37.0 | −3.1 | 12.374 | −10.788 | −6.414 | 0.850 | 0.100 |

TABLE 3B

| Posterior Lens | | | | |
|---|---|---|---|---|
| Anterior Radius (mm) | Posterior Radius (mm) | Anterior Surface CC | CT (mm) | ET (mm) |
| −6.619 | −23.241 | −2.067 | 0.120 | 0.500 |
| −6.917 | −15.145 | −1.672 | 0.120 | 0.451 |
| −10.790 | −12.819 | −1.922 | 0.120 | 0.207 |

Figure 4:
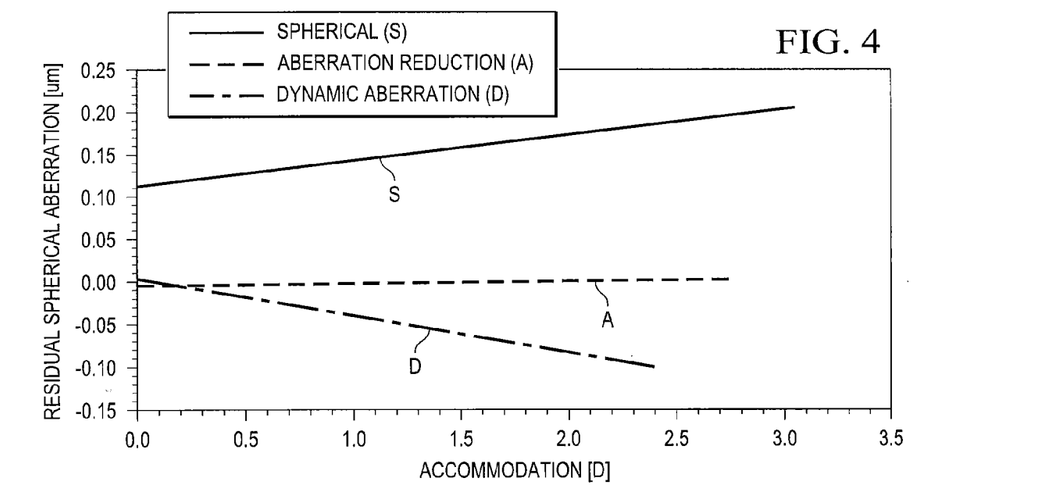
FIG. 4 presents calculated residual spherical aberration of three hypothetical IOL designs as a function of accommodation: a spherical design, a design minimizing spherical aberration, and a design according ton an embodiment of the invention.

FIG. 4 presents theoretically calculated graphs indicating the residual spherical aberration of the above hypothetical designs as a function of accommodation. The graphs indicate that the spherical design exhibits a positive residual spherical aberration at zero accommodation with the spherical aberration increasing with a positive slope as the accommodative power increases. The design with reduced aberration exhibits a substantially constant residual spherical aberration over the calculated change in accommodative power (it exhibits a small positive slope). In contrast, the design in accordance with the teachings of the invention exhibits a small positive residual spherical aberration at zero accommodation with the residual accommodation changing to a negative value as the accommodative power increases beyond a certain value. The residual spherical aberration decreases with a negative slope as the accommodative power further increases. As discussed above, this dynamic change in the spherical aberration with accommodative power provides a number of advantages, including enhancing the effective accommodative power of the lens.

Figure 5:
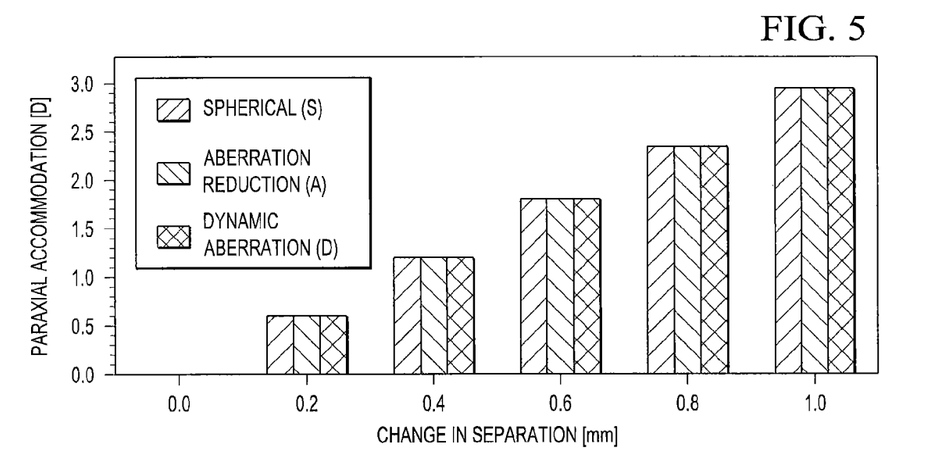
FIG. 5 shows calculated paraxial accommodation provided by three IOL designs (a spherical design, a design minimizing spherical aberration, and a design according ton an embodiment of the invention) at different separation distances of their anterior and posterior lenses relative to one another.

FIG. 5 shows calculated paraxial accommodation provided by the three designs at different separation distances of their anterior and posterior lenses relative to one another. The figure shows that the three designs exhibit similar nominal paraxial accommodation as a function of separation of their elements.

Figure 6A:
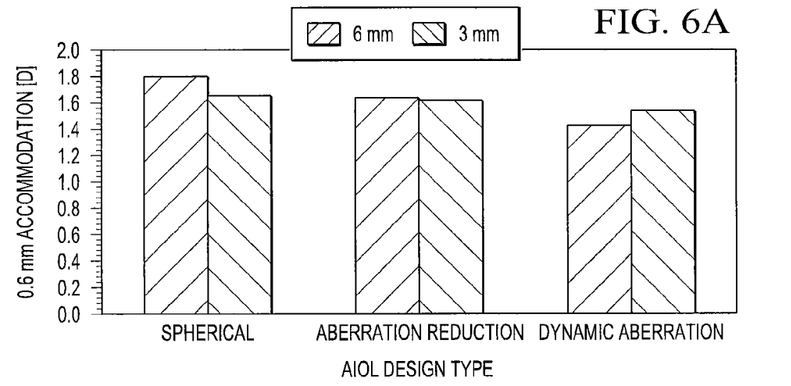
FIG. 6A shows theoretically calculated accommodation by aberration influence for 0.6 mm separation of the anterior and the posterior lenses of three hypothetical dual-optic accommodative IOLs: a spherical design, a design minimizing spherical aberration and a design according to an embodiment of the invention.
Figure 6B:
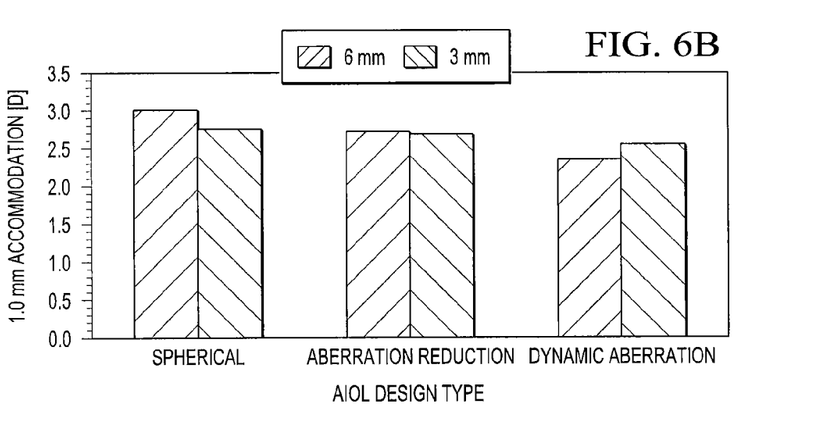
FIG. 6B shows theoretically calculated accommodation by aberration influence for 1 mm separation of the anterior and the posterior lenses of three hypothetical dual-optic accommodative IOLs: a spherical design, a design minimizing spherical aberration and a design according to an embodiment of the invention.

As noted above, the dynamic spherical aberration provided by the design according to the teachings of the invention can, however, lead to an enhanced effective accommodation as the pupil size decreases. By way of illustration, FIGS. 6A and 6B show theoretically calculated accommodation by aberration influence for, respectively, 0.6 mm and 1 mm separation of the anterior and the posterior lenses for the aforementioned three designs. The spherical design shows a decrease in such accommodation, and the design with reduced aberration shows no substantial change, when the pupil diameter decreases from 6 mm to 3 mm. In contrast, this decrease in the pupil diameter leads to an increase in effective accommodative power provided by the dynamic spherical aberration of the design according to the teachings of the invention.

Figure 7A:
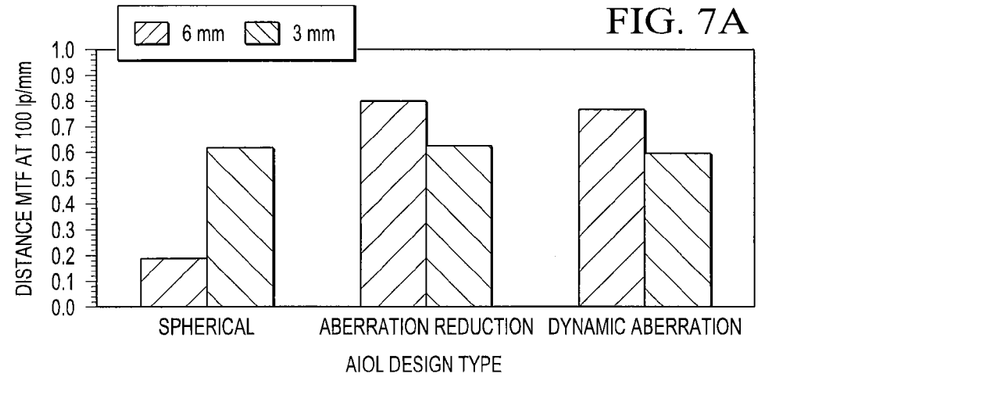
FIG. 7A shows theoretically calculated modulation transfer function (MTF) at 100 lp/mm for distance vision at 6 mm and 3 mm pupil sizes corresponding to three hypothetical dual-optic accommodative IOL designs: a spherical design, a design minimizing spherical aberration and a design according to an embodiment of the invention.

By way of further illustration, FIG. 7A shows theoretically calculated modulation transfer function (MTF) at 100 lp/mm for distance vision corresponding to the afore-mentioned three designs at 6 mm and 3 mm pupil sizes as a measure of the image quality provided by the three lenses. As known to those having ordinary skill in the art, an MTF of an imaging system, such as an IOL, can be defined as a ratio of contrast associated with an image of an object formed by the system relative to a contrast associated with the object. The MTF associated with an optical system generally depends not only on the spatial frequency of the intensity distribution of the light illuminating the imaging system, but it can also be affected by other factors, such as the size of an illumination aperture as well as the wavelength of the illuminating light. In many embodiments, the MTF can be measured and/or calculated for light having a wavelength of about 550 nm—though other wavelengths or a combination of wavelengths can also be employed.

Figure 7B:
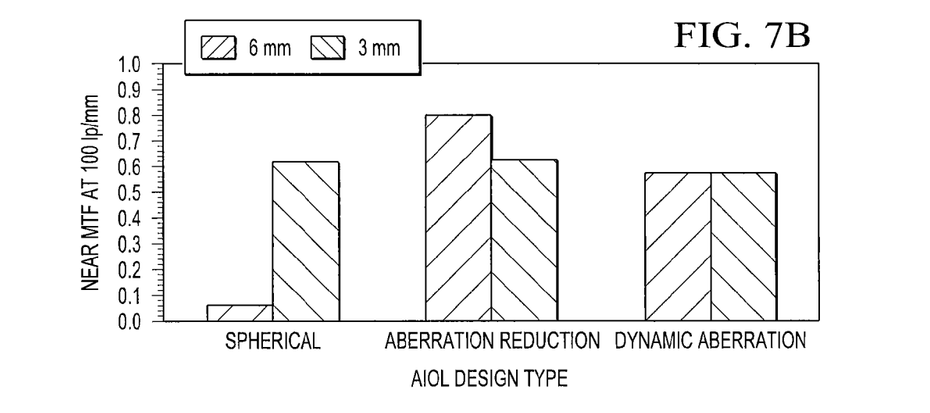
FIG. 7B shows theoretically calculated modulation transfer function (MTF) at 100 lp/mm for near vision at 6 mm and 3 mm pupil sizes corresponding to the three hypothetical dual-optic accommodative IOL designs: a spherical design, a design minimizing spherical aberration and a design according to an embodiment of the invention.

With continued reference to FIG. 7A, the spherical design exhibits poor image quality for a pupil diameter of 6 mm while the theoretical performance of the design having a dynamic spherical aberration is comparable to that of the design exhibiting reduced aberration. FIG. 7B presents theoretically calculated MTF at 100 lp/mm for near vision corresponding to the three designs at 6 mm and 3 mm. Again, the spherical design exhibits a poor image quality at 6-mm pupil diameter. The reduced-aberration and the dynamic aberration designs both exhibit good image quality at both 3-mm and 6-mm pupil diameters with the dynamic-aberration design exhibiting a lower MTF for 6-mm pupil diameter.

Figure 8A:
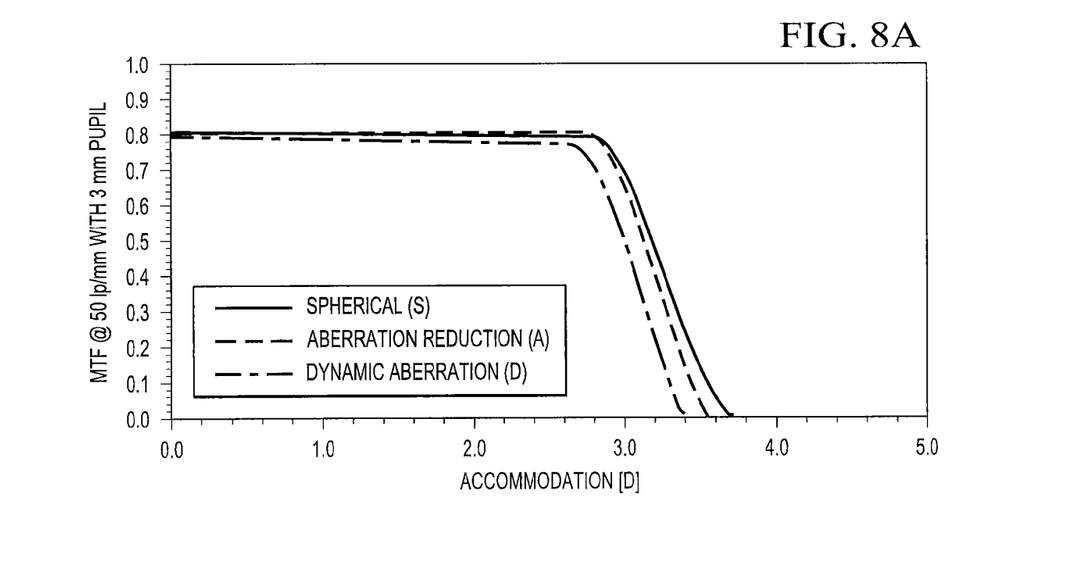
FIG. 8A presents graphs corresponding to calculated MTF at 50 lp/mm for three designs as a function of the accommodation power for a 3-mm pupil diameter: a spherical design, a design minimizing spherical aberration, and a design according ton an embodiment of the invention, FIG. 8B present graphs corresponding to calculated MTF at 50 lp/mm for the three designs as a function of the accommodation power for a 6-mm pupil diameter: a spherical design, a design minimizing spherical aberration, and a design according ton an embodiment of the invention.
Figure 8B:
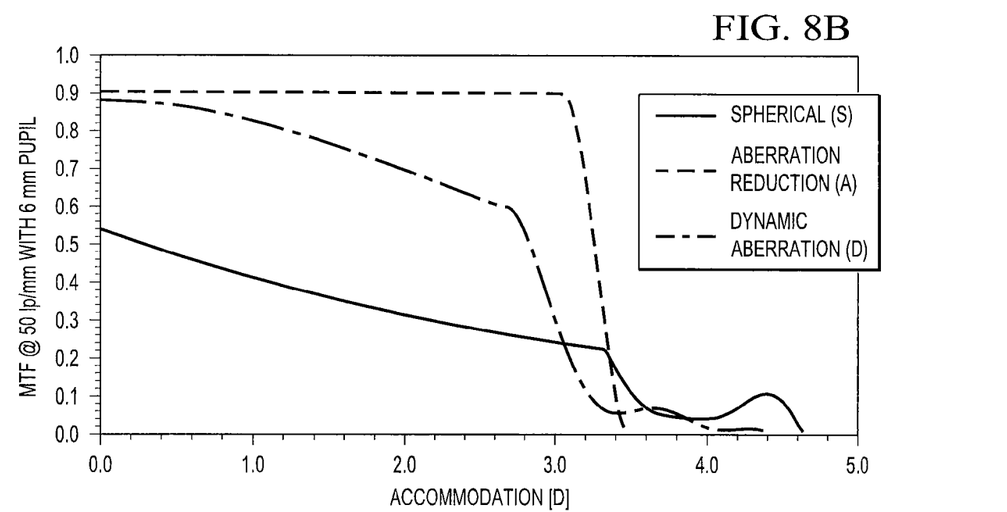

FIGS. 8A and 8B present graphs corresponding to calculated MTF at 50 lp/mm for the three designs as a function of the accommodation power for 3-mm and 6-mm pupil diameters, respectively. For 3-mm pupil size, the depth-of-focus exhibited by the three designs is comparable. For 6-mm pupil size, the three designs exhibit different depth-of-focus with the dynamic aberration design showing an increase the depth of focus, due to the aberrations designed into the system.

Figure 9:
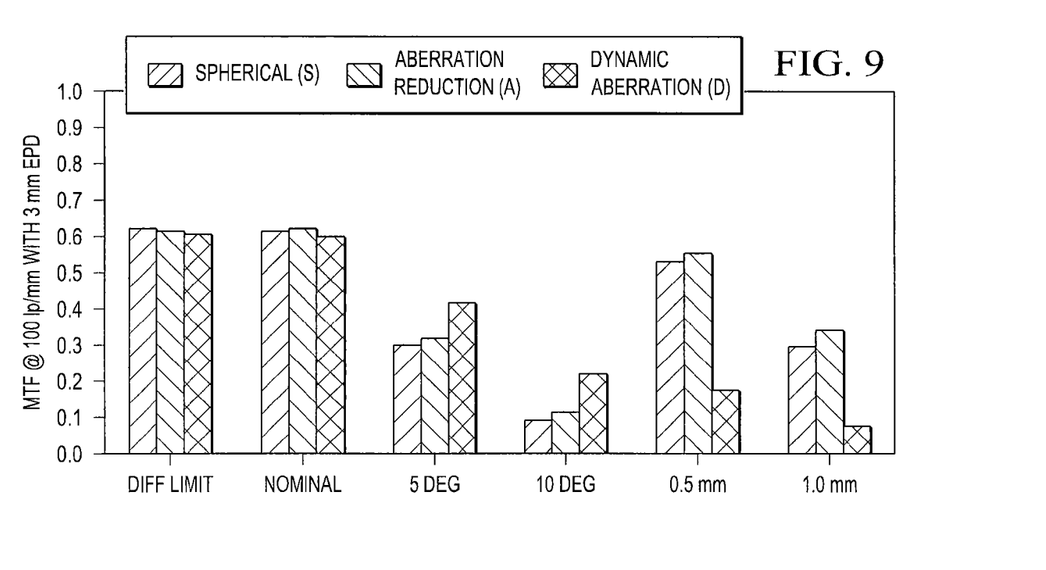
FIG. 9 presents calculated effect of tilt and decentration on image quality of three hypothetical dual-optic accommodative IOL designs: a spherical design, a design minimizing spherical aberration, and a design according to an embodiment of the invention.

FIG. 9 shows calculated effect of tilt and decentration on the image quality of the three designs as defined by calculated MTF corresponding to 100 lp/mm at a pupil diameter of 3 mm. The MTF values for two tilt angles of 5 and 10 degrees and two decentration values of 0.5 mm and 1.0 mm are compared with the nominal and diffraction limited MTF values, indicating that the aberration reduction design demonstrates the greatest robustness to tilt and decentration.

In some embodiments, such as the above examples, the IOLs exhibit the following mechanical constraints: a reasonable edge thickness (e.g., and edge thickness less than about 0.3 mm), and a maximum surface sag of the posterior surface of the posterior element that is less than about 0.5 mm (e.g., less than about 0.36 mm).

Those having ordinary skill in the art will appreciate that various changes can be made to the above embodiments without departing from the scope of the invention.

What is claimed is:

1. An accommodative intraocular lens (IOL) exhibiting a dynamic spherical aberration as a function of accommodative power, said intraocular lens comprising:
    an anterior optical element having at least one aspherical surface, and
    a posterior optical element having at least one aspherical surface,
    a mechanism coupling said anterior and posterior optical elements and allowing axial movement of said elements relative to one another in response to natural accommodative forces of an eye in which the IOL is implanted for providing accommodation when the intraocular lens is implanted in a subject's eye, said mechanism adapted to adjust an axial separation between said elements over a range of about 0 mm to about 2 mm as the accommodation varies from distance vision to near vision,
    wherein said aspherical surfaces of the anterior and posterior elements are adapted to provide a combined spherical aberration that varies with accommodation, wherein said combined spherical aberration varies over a range extending from about +0.20 µm to about −0.50 µm as the accommodation state of the eye varies from one suitable for distance vision to one suitable for near vision.

2. The IOL of claim 1, wherein said IOL exhibits a negative spherical aberration for distance vision with the aberration decreasing as a function of increasing accommodation.

3. The IOL of claim 1, wherein the aspherical surface of at least one of said elements exhibits an asphericity characterized by a conic constant "k" in a range of about −20 to about −60.

4. The IOL of claim 1, wherein said aspherical surface of the anterior optical element corresponds to any of an anterior or a posterior surface of said anterior optical element.

5. The IOL of claim 1, wherein said aspherical surface of the posterior optical element corresponds to any of an anterior or a posterior surface of said posterior optical element.

6. The IOL of claim 1, wherein said anterior optical element provides an optical power in range of about 6 to about 40 Diopters.

7. The IOL of claim 1, wherein said posterior optical element provides an optical power in a range of about 6 to about 40 Diopters.

8. The IOL of claim 1, wherein said anterior and posterior optical elements are formed of a biocompatible material.

9. The IOL of claim 1, wherein at least one said optics has a toric surface.

10. The IOL of claim 1, wherein said spherical aberration exhibits a change characterized by a negative slope as a function of increased accommodation.

11. An accommodative intraocular lens (IOL) exhibiting a dynamic spherical aberration as a function of accommodative power, said intraocular lens comprising:
    an anterior optical element having at least one aspherical surface, and
    a posterior optical element having at least one aspherical surface,
    a mechanism coupling said anterior and posterior optical elements and allowing axial movement of said elements relative to one another in response to natural accommodative forces of an eye in which the IOL is implanted for providing accommodation when the intraocular lens is implanted in a subject's eye, said mechanism adapted to adjust an axial separation between said elements over a range of about 0 mm to about 2 mm as the accommodation varies from distance vision to near vision,
    wherein said aspherical surfaces of the anterior and posterior elements are adapted to provide a combined spherical aberration that varies as a function of pupil size when the lens is implanted in a patient's eye, wherein said combined spherical aberration varies over a range extending from about +0.20 µm to about −0.50 µm as the accommodation state of the eye varies from one suitable for distance vision to one suitable for near vision.

12. The IOL of claim 11, wherein said combined spherical aberration is negative for pupil sizes less than about 6 mm.

13. The IOL of claim 11, wherein said combined spherical aberration is positive for pupil sizes greater than about 1 mm.

14. The IOL of claim 11, wherein said anterior optical element provides a monofocal optical power in a range of about 20 to about 50 Diopters.

15. The IOL of claim 11, wherein said posterior optical element provides a monofocal optical power in a range of about −50 to about −1 Diopters.

16. An accommodative intraocular lens (IOL) exhibiting a dynamic spherical aberration as a function of accommodative power, said intraocular lens comprising:
an anterior optic having at least one aspherical surface,
a posterior optic having at least one aspherical surface,
a mechanism coupling said anterior optic to said posterior optic so as to cause an axial movement of said optics relative to one another in response to natural accommodative forces of an eye in which the IOL is implanted for providing accommodation when the intraocular lens is implanted in a subject's eye, said mechanism adapted to adjust an axial separation between said optics over a range of about 0 mm to about 2 mm as the accommodation varies from distance vision to near vision,
a diffractive structure disposed on at least a surface of one of said optics,
wherein said aspherical surfaces of the anterior and posterior optics are adapted to provide a combined spherical aberration that varies with accommodation and said aspherical surfaces are adapted such that said IOL exhibits a decreasing spherical aberration as a function of increasing axial separation between said optics, wherein said combined spherical aberration varies over a range extending from about +0.20 μm to about −0.50 μm as the accommodation state of the eye varies from one suitable for distance vision to one suitable for near vision.

* * * * *